United States Patent
Huberman

(10) Patent No.: US 8,815,878 B1
(45) Date of Patent: Aug. 26, 2014

(54) SPIRO HEMIAMINALS FOR TREATING VIRAL DISEASES

(75) Inventor: Eliezer Huberman, Chicago, IL (US)

(73) Assignee: NovaDrug, LLC, Chicago, IL (US)

( * ) Notice: Subject to any disclaimer, the term of this patent is extended or adjusted under 35 U.S.C. 154(b) by 274 days.

(21) Appl. No.: 13/191,878

(22) Filed: Jul. 27, 2011

Related U.S. Application Data

(60) Provisional application No. 61/368,843, filed on Jul. 29, 2010.

(51) Int. Cl.
*A61K 31/517* (2006.01)
*C07D 239/72* (2006.01)
*C07D 403/00* (2006.01)

(52) U.S. Cl.
USPC ............... 514/266.1; 514/257; 514/266.2; 514/266.3; 544/283; 544/284; 544/287

(58) Field of Classification Search
USPC ......... 514/257, 266.1, 266.2, 266.3; 544/283, 544/284, 287
See application file for complete search history.

(56) References Cited

PUBLICATIONS

STN registrition file, RN 1381190-52-8, Jul. 4, 2012.*
STN registrition file, RN 1381194-03-1, Jul. 4, 2012.*
STN registrition file, RN 1381742-11-5, Jul. 5, 2012.*
Gordon et al., "Control of Hepatitis C: A Medicinal Chemistry Perspective," *J. Med. Chem.*, 48(1): 1-20 (2005).
Kneteman et al., "Anti-HCV Therapies in Chimeric *scid*-Alb/uPA Mice Parallel Outcomes in Human Clinical Application," *Hepatology*, 43(6): 1346-1353 (2006).
Kneteman et al., "HCV796: A Selective Nonstructural Protein 5B Polymerase Inhibitor with Potent Anti-Hepatitis C Virus Activity In Vitro, in Mice with Chimeric Human Livers, and in Humans Infected with Hepatitis C Virus," *Hepatology*, 49(3): 745-752 (2009).
Lauer et al., "Hepatitis C Virus Infection," *N. Engl. J. Med.*, 345(1): 41-52 (2001).
Mercer et al., "Hepatitis C Virus Replication in Mice with Chimeric Human Livers," *Nat. Med.*, 7(8): 927-933 (2001).
Pathalk et al., "Enzymes and protecting group chemistry," *Curr Opin Chem Biol.*, 2(1):112-20. (1998).
Tan et al., "Hepatitis C Therapeutics: Current Status and Emerging Strategies," *Nat. Rev. Drug Discovery*, 1: 867-881 (2002).

\* cited by examiner

*Primary Examiner* — Shengjun Wang
(74) *Attorney, Agent, or Firm* — Barnes & Thornburg LLP; Alice O. Martin

(57) ABSTRACT

Substituted spiro hemiaminals and methods for their use in the treatment of viral diseases, including hepatitis C viral infections, are described herein.

19 Claims, 2 Drawing Sheets

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggtttagga ttcgtgctca t                                          21

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
caccctatca ggcagtacca caaggcc                                    27

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcggaaccg gtgagtaca                                             19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aggtttagga ttcgtgctca t                                          21

```
<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaaggtgaag gtcggagtc                                                  19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaagatggtg atgggatttc                                                 20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgcggaac cggtgagta                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcaggcagta ccacaaggc                                                  19
```

SPIRO HEMIAMINALS FOR TREATING VIRAL DISEASES

CROSS REFERENCE TO RELATED APPLICATIONS

This patent application claims the benefit of priority under 35 U.S.C. §119(e) to U.S. Provisional Application No. 61/368,843, filed Jul. 29, 2010, the content of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 27, 2011, is named 115189_SEQ_ST25.txt and is 2,048 bytes in size.

TECHNICAL FIELD

The invention described herein pertains to substituted Spiro hemiaminals and methods for their use in treatment of viral diseases including hepatitis C viral infections.

BACKGROUND AND SUMMARY

Hepatitis C (HCV) belongs to the Flaviviridae family of positive-sense, single-stranded RNA viruses. The HCV genome encodes a polyprotein, that includes 3000 amino acid residues, which is processed into both structural and nonstructural proteins. HCV infection is a significant global health issue; the World Health Organization estimates that over 170 million people carry the HCV infection, which can ultimately result in chronic hepatitis, cirrhosis, and hepatocellular carcinoma. It has been reported that those complications are responsible for about 10,000-20,000 deaths annually in the U.S. alone, and that HCV is the leading cause of advanced liver disease and the leading underlying cause for liver transplantation. Current therapies for HCV infection rely on the combination of interferon-α (IFN) and the nonspecific antiviral medication, ribavirin. This treatment regimen reportedly causes undesirable side effects such as leucopenia, thrombocytopenia, and hemolytic anemia, with the added disadvantage that only about 40% of patients achieve a sustained viral response (see, for example, G. M. Lauer, B. D. Walker, N. Engl. J. Med. 2001, 345, 41; C. P. Gordon, P. A. Keller, J. Med. Chem. 2005, 48, 1; S.-L. Tan, A. Pause, Y. Shi, N. Sonenberg, Nat. Rev. Drug Discovery 2002, 1, 867; the foregoing publications, and each additional publication cited herein, are incorporated herein by reference). Thus, more effective and less toxic anti-HCV therapeutics are greatly needed.

It has been discovered that spiro hemiaminals are useful for treating HCV.

In one illustrative embodiment, described herein are substituted Spiro hemiaminals that are effective in the treatment of viral diseases including HCV. In another embodiment, described herein are pharmaceutical compositions comprising the substituted Spiro hemiaminals, and methods for the use of the substituted spiro hemiaminals, including pharmaceutical compositions containing them, in the treatment of viral diseases including HCV.

In another embodiment, described herein is a pharmaceutical composition for treating a viral infection, a composition that includes (a) a therapeutically effective amount of one or more compounds of the formula

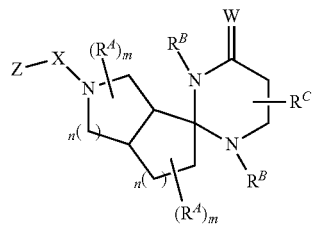

or a pharmaceutically acceptable salt thereof, wherein

X is carbonyl or a derivative thereof, or alkylene, heteroalkylene, alkylenecarbonyl, or heteroalkylenecarbonyl, each of which is optionally substituted;

Z is cycloalkyl, heterocycloalkyl, aryl, or heteroaryl, each of which is optionally substituted;

W is O or S;

RA is independently selected in each instance from the group consisting of H, and alkyl and heteroalkyl, each of which is optionally substituted; where m is independently selected in each instance from the group consisting of 1, 2, and 3;

RB is independently selected in each instance from the group consisting of H, alkyl, heteroalkyl, and a prodrug group;

RC is H; or RC is 1 or 2 substituents independently selected from the group consisting of alkyl, heteroalkyl, cycloalkyl, heterocycloalkyl, aryl, heteroaryl, arylalkyl, heteroarylalkyl, arylheteroalkyl, or heteroarylheteroalkyl, each of which is optionally substituted; or $R^C$ represents a fused cycloalkyl, heterocycloalkyl, aryl, or heteroaryl, each of which is optionally substituted; and n is independently selected in each instance from the group consisting of 1, 2, and 3; and (b) one or more pharmaceutically acceptable carriers, diluents, or excipients, or a combination thereof.

In another embodiment, described herein is a composition as described above wherein X is carbonyl or a derivative thereof.

In another embodiment, described herein is a composition as described above wherein X is alkylene or heteroalkylene, each of which is optionally substituted.

In another embodiment, described herein is a composition as described above wherein X is alkylenecarbonyl or heteroalkylenecarbonyl, each of which is optionally substituted.

In another embodiment, described herein is a composition as described above wherein X is alkylene, each of which is optionally substituted.

In another embodiment, described herein is a composition as described above wherein X is methylene.

In another embodiment, described herein is a composition as described above wherein Z is aryl or heteroaryl, each of which is optionally substituted.

In another embodiment, described herein is a composition as described above wherein Z is monocyclic aryl or heteroaryl, each of which is optionally substituted.

In another embodiment, described herein is a composition as described above wherein Z is bicyclic aryl or heteroaryl, each of which is optionally substituted.

In another embodiment, described herein is a composition as described above wherein W is O.

In another embodiment, described herein is a composition as described above wherein m is independently selected in each instance from the group consisting of 1 and 2.

In another embodiment, described herein is a composition as described above wherein m is 1 in each instance.

In another embodiment, described herein is a composition as described above wherein each RA is H.

In another embodiment, described herein is a composition as described above wherein each RB is independently H or a prodrug group.

In another embodiment, described herein is a composition as described above wherein each $R^B$ is H.

In another embodiment, described herein is a composition as described above wherein RC represents a fused cycloalkyl, heterocycloalkyl, aryl, or heteroaryl, each of which is optionally substituted.

In another embodiment, described herein is a composition as described above wherein RC represents a fused optionally substituted aryl or optionally substituted aryl heteroaryl.

In another embodiment, described herein is a composition as described above wherein $R^C$ represents a fused optionally substituted aryl.

In another embodiment, described herein is a composition as described above wherein n is independently selected in each instance from the group consisting of 1 and 2.

In another embodiment, described herein is a composition as described above wherein n is 1 in each instance.

In another embodiment, described herein is a composition as described above wherein the compound has the following relative stereochemistry

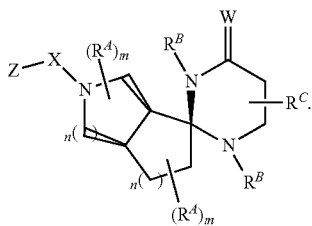

In another embodiment, described herein is a composition as described above wherein the compound has the following absolute stereochemistry

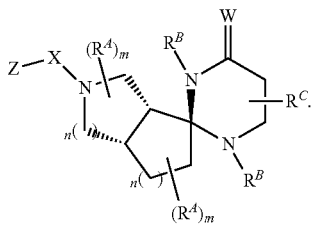

In another embodiment, described herein is a method for treating a viral infection in a patient, the method comprising the step of administering to the patient a therapeutically effective amount of one or more of the compounds described above, or a therapeutically effective amount of one or more of the compositions described above.

In another embodiment, described herein is the use in the manufacture of a medicament for treating a viral infection (a) a therapeutically effective amount of one or more of the compounds described above; or (b) a therapeutically effective amount of one or more of the compositions described above.

In another embodiment, described herein is the composition, method, or use as described above wherein the viral infection is a hepatitis C viral infection.

In addition, various genera and subgenera of each of X, Z, W, RA, RB, RC, and n are described herein. It is to be understood that all possible combinations of the various genera and subgenera of each of X, Z, W, RA, RB, RC, and n described herein represent additional illustrative embodiments of compounds of the invention described herein. It is to be further understood that each of those additional illustrative embodiments of compounds may be used in any of the compositions, methods, and/or uses described herein.

In another embodiment, pharmaceutical compositions containing one or more of the compounds are also described herein. In another embodiment, pharmaceutical compositions are in the form of a unitary dose, unit dose, or unit dosage form. the In one aspect, the compositions, such as unit doses or unit dosage forms, include a therapeutically effective amount of the one or more compounds for treating a patient with HCV. It is to be understood that the compositions may include other components and/or ingredients, including, but not limited to, other therapeutically active compounds, and/or one or more carriers, diluents, excipients, and the like. In another embodiment, methods for using the compounds and pharmaceutical compositions for treating patients with HCV are also described herein. In one aspect, the methods include the step of administering one or more of the compounds and/or compositions described herein to a patient with HCV. In another aspect, the methods include administering a therapeutically effective amount of the one or more compounds and/or compositions described herein for treating patients with HCV. In another embodiment, uses of the compounds and compositions in the manufacture of a medicament for treating patients with HCV are also described herein. In one aspect, the medicaments include a therapeutically effective amount of the one or more compounds and/or compositions for treating a patient with HCV.

It is to be understood that the compounds described herein may be used alone or in combination with other compounds useful for treating HCV, including those compounds that may be therapeutically effective by the same or different modes of action. In addition, it is to be understood that the compounds described herein may be used in combination with other compounds that are administered to treat other symptoms of HCV.

DETAILED DESCRIPTION

Figure 1:
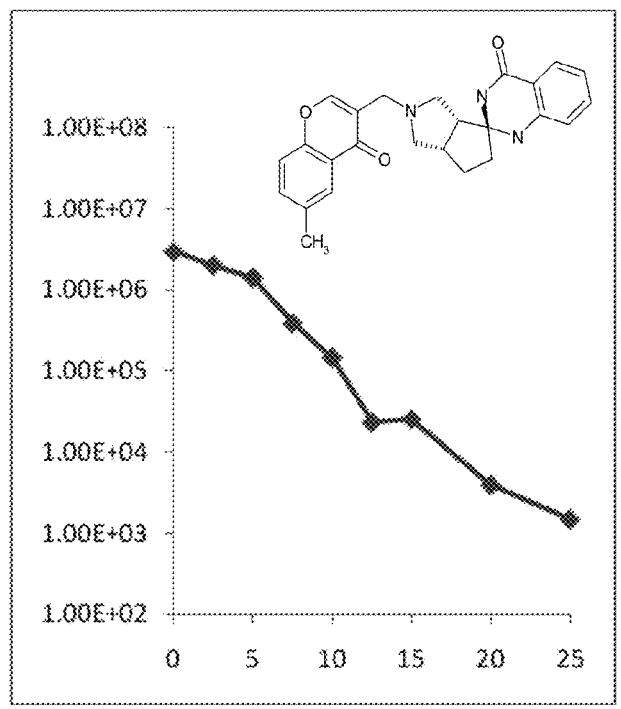
FIGS. 1-3 shows the intracellular HCV RNA levels when cultures were incubated with the test compounds at the doses shown. Each test compound shows a dose response. Without being bound by theory, it is believed herein that when HCV RNA levels are compared among the samples, the data may indicate that the test compounds caused a dose dependent decrease in HCV RNA levels relative to the mock-treated (no compound added) HCV infected control. In each of the compounds shown, it is to be understood that each atom includes a full valence, where the remaining atoms are hydrogens.
Figure 2:
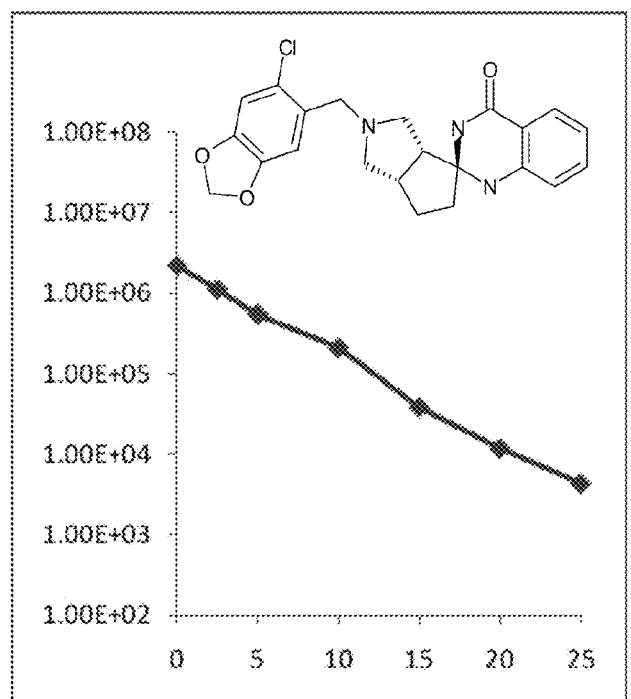
Figure 3:
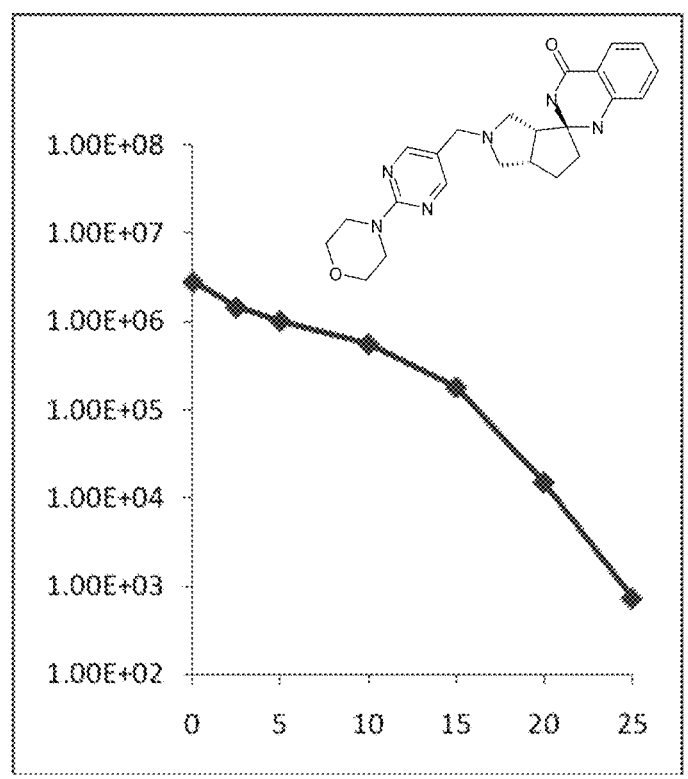

In one embodiment, the methods and compositions described herein include a therapeutically effective amount of one or more compounds of the formula:

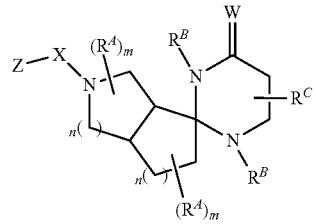

or a pharmaceutically acceptable salt thereof, wherein
X is carbonyl or a derivative thereof, or alkylene, heteroalkylene, alkylenecarbonyl, or heteroalkylenecarbonyl, each of which is optionally substituted;

Z is cycloalkyl, heterocycloalkyl, aryl, or heteroaryl, each of which is optionally substituted;

W is O or S;

RA is independently selected in each instance from the group consisting of H, and alkyl and heteroalkyl, each of which is optionally substituted; where m is independently selected in each instance from the group consisting of 1, 2, and 3;

$R^B$ is independently selected in each instance from the group consisting of H, alkyl, heteroalkyl, and a prodrug group;

RC is H; or RC is 1 or 2 substituents independently selected from the group consisting of alkyl, heteroalkyl, cycloalkyl, heterocycloalkyl, aryl, heteroaryl, arylalkyl, heteroarylalkyl, arylheteroalkyl, or heteroarylheteroalkyl, each of which is optionally substituted; or $R^C$ represents a fused cycloalkyl, heterocycloalkyl, aryl, or heteroaryl, each of which is optionally substituted; and n is independently selected in each instance from the group consisting of 1, 2, and 3.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

In each of the foregoing and following embodiments, derivatives are also described. Illustrative derivatives include, but are not limited to, those compounds that may be synthetically prepared from the compounds described herein, as well as those compounds that may be prepared in a similar way as those described herein, but differing in the selection of starting materials. For example, described herein are compounds that include various functional groups on aromatic rings. It is to be understood that derivatives of those compounds also include the compounds having for example different functional groups on those aromatic rings than those explicitly set forth in the definition of substituents on the compounds. In addition, it is to be understood that derivatives of those compounds also include the compounds having those same or different functional groups at different positions on the aromatic ring. Similarly, derivatives include parallel variations of other functional groups on the compounds described herein.

It is to be understood that such derivatives may include prodrugs of the compounds described herein, compounds described herein that include one or more protection or protecting groups, including compounds that are used in the preparation of other compounds described herein.

In addition, the compounds described herein may also include prodrug groups, and including the corresponding prodrugs of the various derivatives thereof. In addition, the compounds described herein may be amorphous as well as be any and all morphological forms. In addition, the compounds described herein may be in the form of solvate, including hydrates, or other solvates.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "carbonyl and derivatives thereof" includes the group C(O), C(S), C(NH) and substituted amino derivatives thereof As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical —$(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles. It is to be understood that the unit doses and/or unit dosage forms described herein may be single or divided. It is also to be understood that the unit doses and/or unit dosage forms may be administered using a variety of daily, weekly, monthly, or quarterly dosing protocols. Examples of dosing protocols include q.d., b.i.d., t.i.d., or even every other day, once a week, twice a week, once a month, once a quarter, and the like. In each of these cases it is understood that the daily, weekly, month, or quarterly dose instance corresponds to the therapeutically effective amounts described herein. In addition, it is to be understood that when a divided dose is administered, the corresponding therapeutically effective amounts are the totals of the divided dose.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

The effective use of the compounds, compositions, and methods described herein for treating or ameliorating one or more effects of HCV using one or more compounds described herein may be based upon animal models, such as murine, canine, porcine, and non-human primate animal models of disease. For example, it is understood that HCV in humans may be characterized by a loss of function, and/or the development of symptoms, each of which may be elicited in animals, such as mice, and other surrogate test animals. Such animal models may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to limit invention.

EXAMPLE

Test Compounds. Illustrative substituted Spiro hemiaminals described herein are obtained from commercial suppliers (>90% purity) and used as obtained.

METHOD EXAMPLE

Chimeric Mouse Model. The animals used are homozygous albumin (Alb)-urokinase plasminogen activator (uPA)/severe combined immunodeficient (SCID) mice, and are housed in a virus-free/antigen-free environment until ready for use. The mouse model used herein is similar to those previously described (see, for example, N. M. Kneteman Et Al., Hepatology, 2006, 43, 1346; N. M. Kneteman Et Al., Hepatology, 2009, 49, 745).

Isolation and Transplantation of Human Hepatocytes. Segments of human liver tissue (~20 $cm^3$) are flushed with cold phosphate-buffered saline and rapidly transported to the tissue isolation laboratory. Hepatocytes are isolated and purified using collagenase-based perfusion with 0.38 mg/ml Liberase CI solution (Boehringer Mannheim), using previously described techniques (Mercer Df, Et Al., Hepatitis C Virus Replication in Mice with Chimeric Human Livers, Nat. Med. 2001, 7, 927-933). Recipient mice (5-14 days old uPA/SCID mice) are anesthetized with halothane/$O_2$, and $1\times10^6$ viable hepatocytes are injected into the inferior pole of the spleen. The hepatocytes then transit on their own to the liver where they implant and expand.

Human α-1 Antitrypsin Analysis. Human α-1 antitrypsin (hAAT) analysis is used to confirm stable ongoing function of the human hepatocyte grafts and to determine whether any change in HCV titer is attributable to hepatocyte death or injury. Mouse serum is analyzed by sandwich enzyme-linked immunosorbent assay as previously described (N. M. Kneteman Et Al., Hepatology, 2006, 43, 1346). Briefly, samples of mouse serum (2 ul) are diluted 1/100 in blocking buffer and analyzed by sandwich ELISA using a polyclonal goat anti-human alpha1-antitrypsin (hAAT) antibody (#81902, Diasorin, Stillwater Minn.) as the capturing antibody. A portion of the same antibody is cross-linked to horseradish peroxidase (#31489, Pierce, Rockford, Ill.) and used as the secondary antibody, with signal detection by 3,3',5,5'-tetramethylbenzidine (Sigma, St. Louis, Mo.).

HCV Isolation and Quantitation. Murine serum analysis is performed in blinded fashion using the Cobas Amplicor HCV Monitor system (Roche Diagnostics). Lower limit of quantification is 600 IU/mL. Viral RNA is extracted using Buffer AVL from Qiagen (19073) according to the manufacturer's instructions. The RNA is transcribed to cDNA with a HCV specific primer (5'-AGGTTTAGGATTCGTGCTCAT) (SEQ ID NO: 1) with a High Capacity RNA to cDNA kit (Applied Biosystems, #4369016) according to the manufacturer's directions. RT-PCR is performed using an ABI 7300 Real Time PCR system and Taqman chemistry, with all measurements done in duplicate. 6-FAM-CACCCTATCAGGCAG-TACCACAAGGCC-TAMRA (SEQ ID NO: 2) is used as the HCV specific detection probe and a primer set detecting the conserved 5'UTR region of HCV (5'-TGCGGAACCGGT-GAGTACA (SEQ ID NO: 3), 5'-AGGTTTAGGATTCGT-GCTCAT (SEQ ID NO: 4)). For absolute quantitation, a standard curve of known dilutions of a plasmid containing the sequence for HCV variant H77c (pCV-H77c) is created, alongside an Optiquant HCV RNA high control (Optiquant).

Experimental Conduct. Six weeks after hepatocyte transplantation, mice are screened for serum hAAT, and animals above a 100-μg/ml cutoff are inoculated by intraperitoneal injection with 100 μg genotype 1a HCV-laden human serum (approximately $2\times10^5$ copies/ml). Baseline HCV levels are obtained at 1 and 2 weeks after inoculation, and mice with titers above $2\times10^4$ copies/mL are allocated to experimental groups. Allocation sought to balance groups for HCV titers, hAAT levels, sex, and weight with decreasing priority.

METHOD EXAMPLE

The following protocol is used for the evaluation of PK parameters and tolerance of the animals for the study drug. The protocol includes three escalating dose levels for each of the compounds administered at a volume of 5 mL/kg once a day by intra-peritoneal injection. The tolerance is determined over a fourteen day treatment course. The study animals include three 5-mouse groups. Also included is one 5-mouse control group injected with 5 mL/kg of vehicle. The mouse groups include both male and female 3-month old murine KMT Mice™ with a weight range of ≥12.0 g. Blood samples are drawn via the central tail artery of the animal for measurement of serum concentrations of the substituted Spiro hemiaminals on the morning of Day 8 immediately prior to the drug dose (trough sample 24 hours post the Day 7 dose) and on the morning of Day 15 (trough sample 24 hours post the final Day 14 dose). A volume of approximately 100 μL is collected into tubes, allowed to clot at 2-8° C., centrifuged, and the serum removed from above the clot pellet and stored frozen at −80° C. until ready for concentration measurement.

METHOD EXAMPLE

The following protocol is used for efficacy evaluation of the substituted Spiro hemiaminals against HCV infection. The protocol includes three dose levels that are selected based on the tolerability and PK results from the first study described in the previous Method. The efficacy of the substituted spiro hemiaminals is determined over a fourteen day treatment course and seven day follow-up period employing three escalating dose levels of drug administered at a volume of 5 mL/kg once a day by intraperitoneal injection. The baseline animal acceptance criteria are as follows: minimum hAAT value=80; minimum HCV value=$1\times10^4$ IU/ml; health status cutoff≤1-2. The study animals include three 5-mouse groups. Also included is one 5-mouse control group injected with 5 mL/kg of vehicle. The mouse groups include both male and female 3-month old murine KMT Mice™ with a weight range of ≥12.0 g. Blood samples are drawn via the central tail artery for measurement of baseline serum concentrations of hAAT and HCV on Day 3. Subsequent blood draws are made the morning of Day 7, immediately prior to drug dosing, the morning of Day 14, twenty-four hours after the final drug dose administered at approximately 0800 h the previous day and on Day 21, seven days after the last drug dose. A volume of approximately 100 μl is collected into tubes, allowed to clot at 2-8° C., centrifuged and the serum removed from above the clot pellet. Serum samples are stored frozen at −80° C. until ready for testing for HCV and hAAT levels.

EXAMPLE

Assay for Anti-HCV Efficacy of the compounds described herein. In the past, HCV studies involved mainly infected patients and chimpanzees. Recently, a robust HCV infection system was developed with cells derived from the Huh-7 human hepatoma cell line. It is based on the unique JFH-1 HCV consensus cDNA derived from an HCV patient. Using reverse genetics, the infectious virus can be rescued from this HCV clone. The recovered viable JFH virus can be passaged serially in Huh-7 cells. For this reason, this system is amenable for testing the activity of potential drugs for their anti-HCV efficacy. The antiviral activity of the compounds herein are tested in this system.

Initially, 6×103 Huh7-1 cells are incubated overnight in each well of collagen-coated BioCoat 96-well plates (BD Biosciences, Bedford, Mass.) in 0.2 ml 10% medium composed of Dulbecco's modified Eagle's medium supplemented with 10% fetal bovine serum. Subsequently, at 2 day intervals, the cultures are replenished with fresh 0.2 ml 10% medium. After the cultures become confluent, they continue to be replenished at 2 day intervals with fresh 0.2 ml 10% medium that also includes 1% dimethyl sulfoxide (DMSO). After 20 days of these replenishments, the Huh7-1 cultures are incubated with fresh 1% medium (same as 10% medium except that the serum level is 1%) containing HCV at a multiplicity of infection (MOI) of 0.05 focus forming units (ffu)/cell. The HCV (JFH-1 wt Huh7) stock titer is $1.5 \times 10^5$ ffu/ml. The next day (day 1 post-infection) and 2 days later (day 3 post-infection) the media are replenished with fresh 1% medium containing the test compounds dissolved in DMSO. On the 5th day of treatment with the compounds, cell lysates are collected for RNA isolation and Real Time-quantitative Reverse Transcription Polymerase Chain Reaction (RT-qPCR) and culture media are collected for cytotoxicity analysis.

Total RNA is isolated from cells by the guanidine thiocyanate method using standard protocols. One μg RNA is used for cDNA synthesis using TaqMan reverse transcription reagents (Applied Biosystems, Foster City, Calif.) followed by real-time PCR using an Applied Biosystems 7300 real-time thermocycler. Thermal cycling consists of initial denaturation of 10 min at 95° C. followed by 40 cycles of denaturation (15 s at 95° C.) and annealing/extension (1 m at 60° C.). HCV and human glyceraldehyde-3-phosphate dehydrogenase (GAPDH) RNA levels are determined relative to a standard curve of serial dilutions of plasmid containing JFH-1 HCV or GAPDH cDNA. The PCR primers used to detect GAPDH and HCV are: GAPDH (NMX002046) 5'-GAAGGTGAAGGTCGGAGTC-3' (sense) (SEQ ID NO: 5) and 5'-GAAGATGGTGATGGGATTTC-3' (anti-sense) (SEQ ID NO: 6) JFH-1 HCV (AB047639) 5'-TCTGCGGAACCGGTGAGTA-3'(sense) (SEQ ID NO: 7) and 5'-TCAGGCAGTACCACAAGGC-3' (anti-sense) (SEQ ID NO: 8).

METHOD EXAMPLE

HCV Induced Cytotoxicity Test. To determine whether the compounds described herein are cytotoxic at the tested doses used, the Promega CytoTox 96 Non-Radioactive Cytotoxicity Assay kit (Promega, Madison, Wis.) is used. This kit measures lactate dehydrogenase (LDH) levels in the culture medium, which is released from cells due to plasma membrane integrity loss or necrosis. For this test, 50 uL samples of culture medium are collected from the same 5 day cultures used to examine the RNA levels shown previously. The compounds described herein are not generally cytotoxic at the tested doses, and do not generally cause apparent Huh7-1 cell damage. Compounds 3, 4, and 6 showed little to no toxicity in the assay in the concentration ranges of 2.5 to 20 μM. Compounds 3 and 6 showed limited toxicity in the assay at 25 μM.

METHOD EXAMPLE

Joint Treatment for HCV Infection. Effective treatment of HCV infected patients has been reported to require both RBV and IFN-β-1b because that combination is more potent than each drug on its own. The compounds described herein are tested to determine whether they increase the efficacy of either RBV, IFN-β-1b, or a combination thereof. Using the protocol described for determining chemical-evoked reduction in intracellular HCV RNA, the cells are treated with and without 10 U/mL IFN-β-1b in combination with 2.5 or 10 uM of the compounds described herein and for comparison with 10 uM MA and 80 uM RBV.

EXAMPLE

The following compounds are described herein:

| Example No. | COMPOUND |
|---|---|
| 1 | (structure) |
| 2 | (structure) |

| Example No. | COMPOUND |
|---|---|
| 3 | 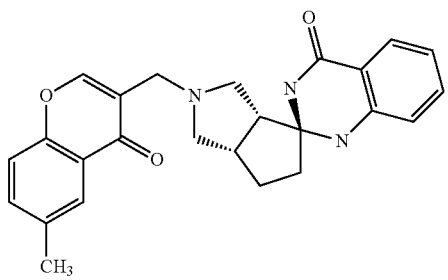 [SMILES: Cc1ccc2occ(CN3C[C@H]4CC[C@]5(NC(=O)c6ccccc6N5)[C@H]4C3)c(=O)c2c1] |
| 4 | 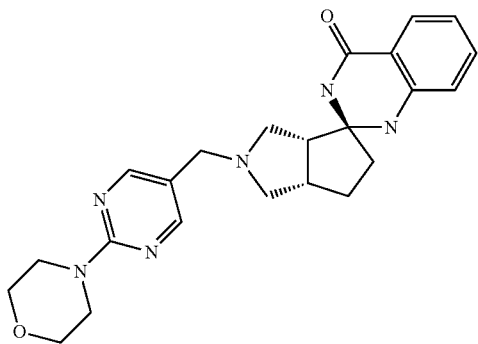 [SMILES: O=C1N[C@]2(CC[C@@H]3CN(Cc4cnc(N5CCOCC5)nc4)C[C@@H]32)Nc2ccccc21] |
| 5 | 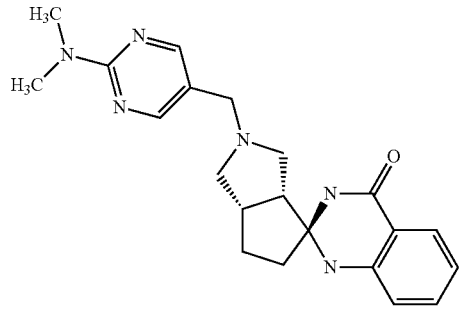 [SMILES: CN(C)c1ncc(CN2C[C@H]3CC[C@]4(NC(=O)c5ccccc5N4)[C@H]3C2)cn1] |
| 6 | 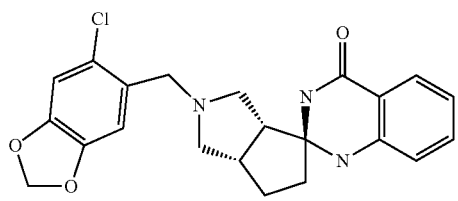 [SMILES: O=C1N[C@]2(CC[C@@H]3CN(Cc4cc5c(cc4Cl)OCO5)C[C@@H]32)Nc2ccccc21] |
| 7 | 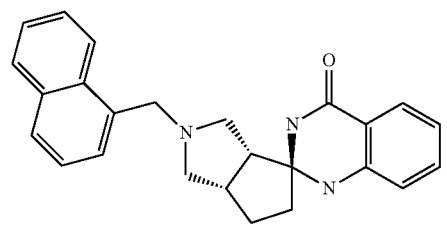 [SMILES: O=C1N[C@]2(CC[C@@H]3CN(Cc4cccc5ccccc45)C[C@@H]32)Nc2ccccc21] |
| Example No. | COMPOUND |
|---|---|
| 8 | 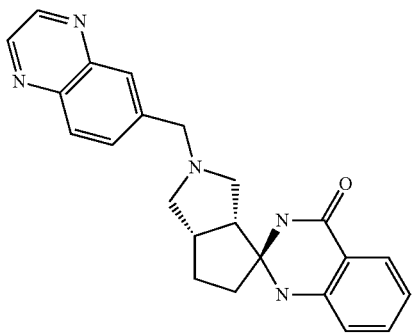 [SMILES: O=C1N[C@]2(CC[C@@H]3CN(Cc4ccc5nccnc5c4)C[C@@H]32)Nc2ccccc21] |
| 9 | 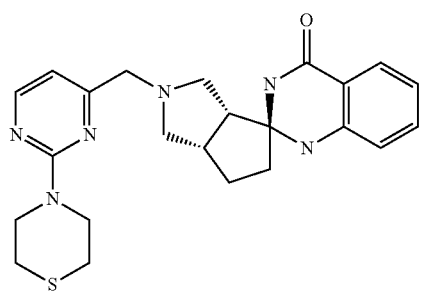 [SMILES: O=C1N[C@]2(CC[C@@H]3CN(Cc4ccnc(N5CCSCC5)n4)C[C@@H]32)Nc2ccccc21] |
| 10 | 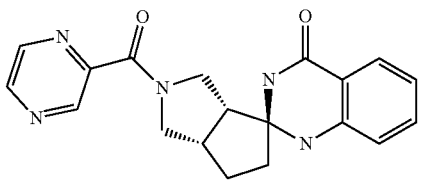 [SMILES: O=C1N[C@]2(CC[C@@H]3CN(C(=O)c4cnccn4)C[C@@H]32)Nc2ccccc21] |
| 11 | 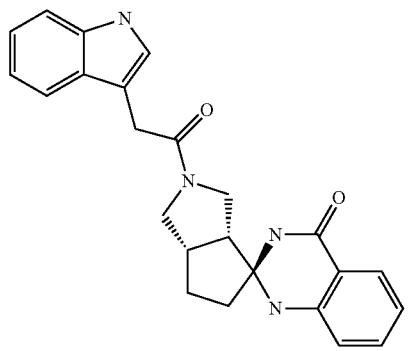 [SMILES: O=C1N[C@]2(CC[C@@H]3CN(C(=O)Cc4c[nH]c5ccccc45)C[C@@H]32)Nc2ccccc21] |
| 12 | |

| Example No. | COMPOUND |
|---|---|
| 13 |  |
| 14 | |
| 15 | |
| 16 | |
| 17 | |
| 18 | |
| Example No. | COMPOUND |
|---|---|
| 19 |  |
| 20 | |
| 21 | |
| 22 | |
| 23 | |

-continued
| Example No. | COMPOUND |
|---|---|
| 24 | 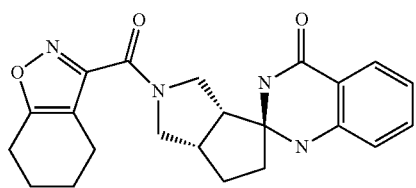 |
| 25 | 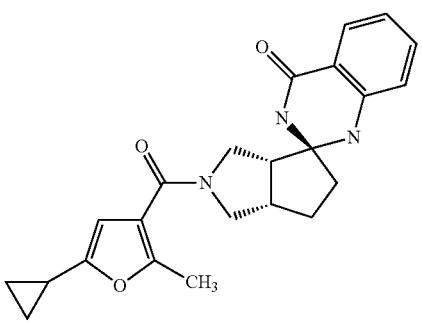 [SMILES: Cc1oc(C2CC2)cc1C(=O)N1C[C@H]2CC[C@]3(NC(=O)c4ccccc4N3)[C@H]2C1] |
| 26 | 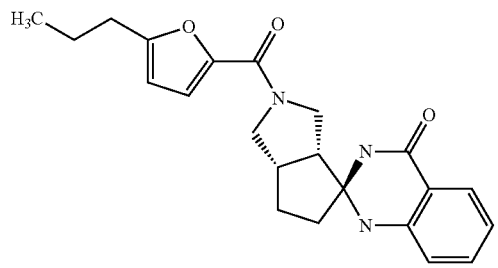 [SMILES: CCCc1ccc(C(=O)N2C[C@H]3CC[C@]4(NC(=O)c5ccccc5N4)[C@H]3C2)o1] |
| 27 | 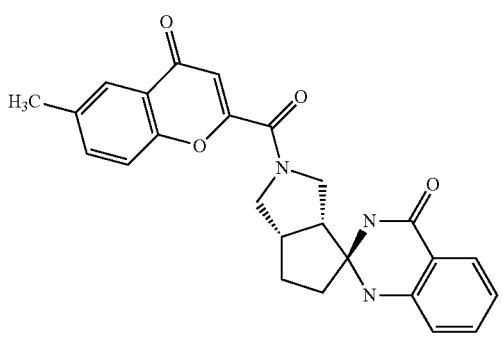 [SMILES: Cc1ccc2oc(C(=O)N3C[C@H]4CC[C@]5(NC(=O)c6ccccc6N5)[C@H]4C3)cc(=O)c2c1] |
| 28 | 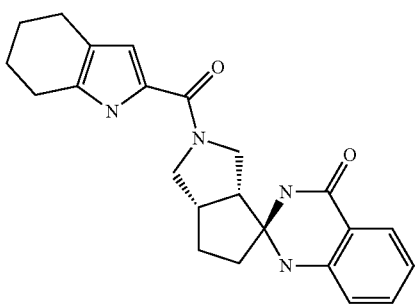 [SMILES: O=C1N[C@]2(CC[C@@H]3CN(C(=O)c4cc5c([nH]4)CCCC5)C[C@@H]32)Nc2ccccc21] |
-continued
| Example No. | COMPOUND |
|---|---|
| 29 | 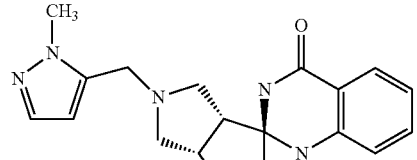 |
| 30 | 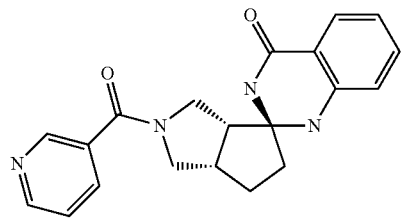 [SMILES: O=C1N[C@]2(CC[C@@H]3CN(C(=O)c4cccnc4)C[C@@H]32)Nc2ccccc21] |
| 31 | 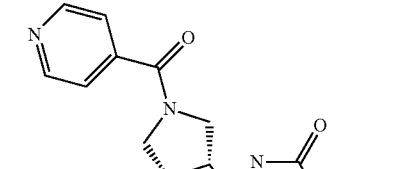 |
| 32 | 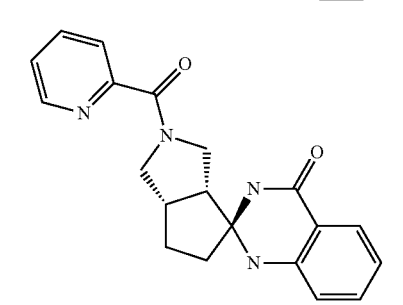 [SMILES: O=C1N[C@]2(CC[C@@H]3CN(C(=O)c4ccccn4)C[C@@H]32)Nc2ccccc21] |
| 33 |  |
| 34 |  |

-continued
| Example No. | COMPOUND |
|---|---|
| 35 | 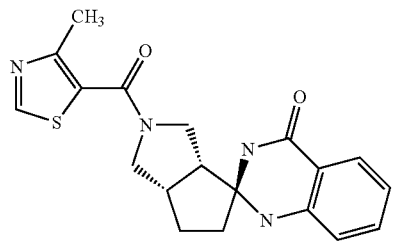 [SMILES: Cc1ncsc1C(=O)N1C[C@H]2CC[C@]3(NC(=O)c4ccccc4N3)[C@H]2C1] |
| 36 | 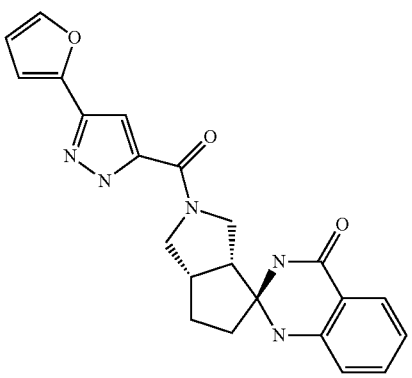 [SMILES: O=C1N[C@]2(CC[C@@H]3CN(C(=O)c4cc(-c5ccco5)n[nH]4)C[C@@H]32)Nc2ccccc21] |
| 37 | 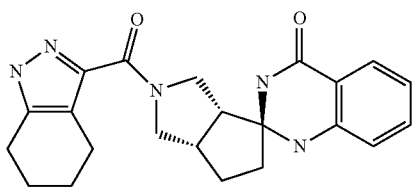 [SMILES: O=C1N[C@]2(CC[C@@H]3CN(C(=O)c4n[nH]c5c4CCCC5)C[C@@H]32)Nc2ccccc21] |
| 38 | 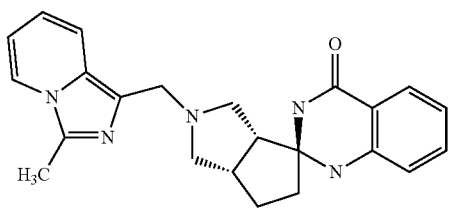 [SMILES: Cc1nc(CN2C[C@H]3CC[C@]4(NC(=O)c5ccccc5N4)[C@H]3C2)c2ccccn12] |
| 39 | 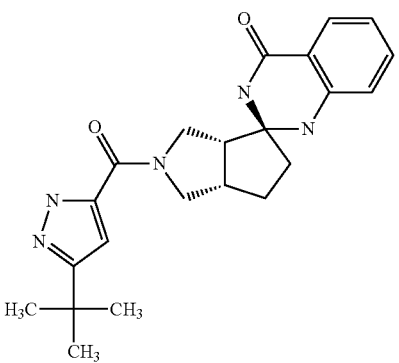 [SMILES: CC(C)(C)c1cc(C(=O)N2C[C@H]3CC[C@]4(NC(=O)c5ccccc5N4)[C@H]3C2)[nH]n1] |
-continued
| Example No. | COMPOUND |
|---|---|
| 40 | 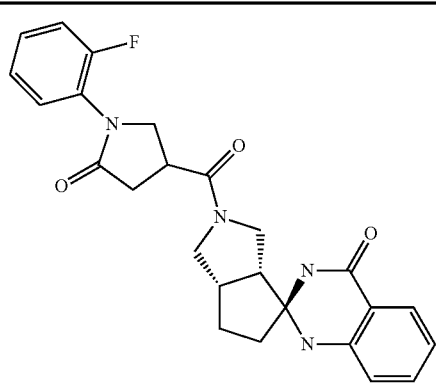 |
| 41 | 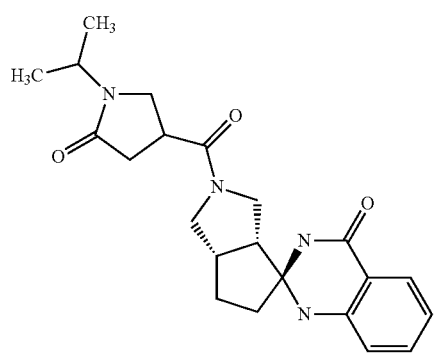 [SMILES: CC(C)N1CC(C(=O)N2C[C@H]3CC[C@]4(NC(=O)c5ccccc5N4)[C@H]3C2)CC1=O] |
| 42 | 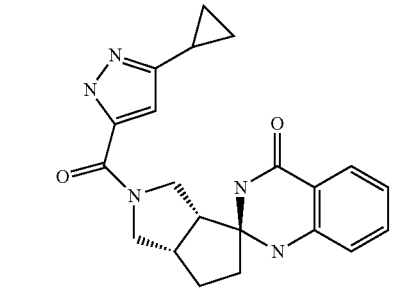 [SMILES: O=C1N[C@]2(CC[C@@H]3CN(C(=O)c4cc(C5CC5)n[nH]4)C[C@@H]32)Nc2ccccc21] |
| 43 | 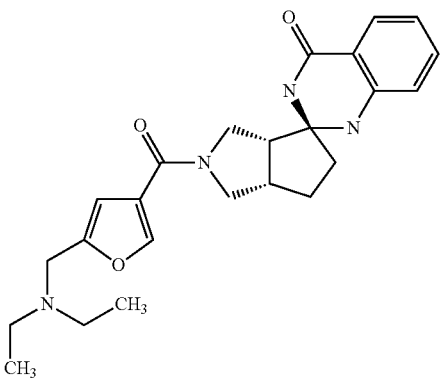 [SMILES: CCN(CC)Cc1cc(C(=O)N2C[C@H]3CC[C@]4(NC(=O)c5ccccc5N4)[C@H]3C2)co1] |

-continued

| Example No. | COMPOUND |
|---|---|
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |

| Example No. | COMPOUND |
|---|---|
| 54 | 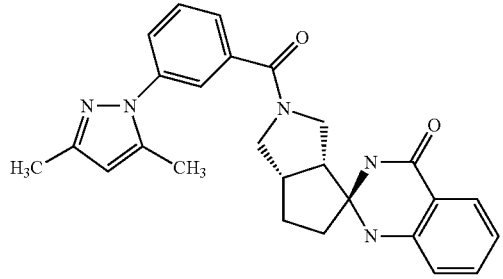 [SMILES: Cc1cc(C)n(-c2cccc(C(=O)N3C[C@H]4CC[C@]5(NC(=O)c6ccccc6N5)[C@H]4C3)c2)n1] |
| 55 | 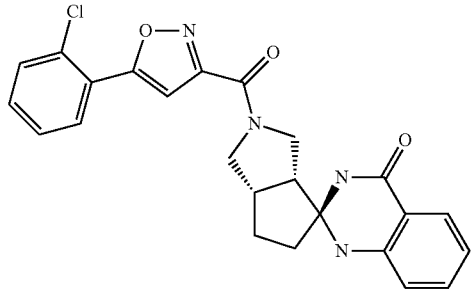 [SMILES: O=C1N[C@]2(CC[C@@H]3CN(C(=O)c4cc(-c5ccccc5Cl)on4)C[C@@H]32)Nc2ccccc21] |
| 56 | 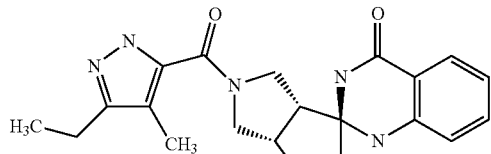 |
| 57 | 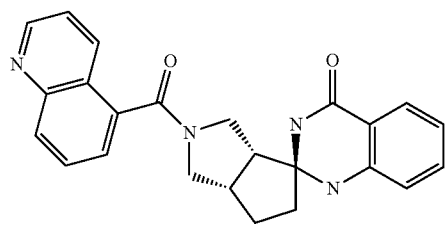 [SMILES: O=C1N[C@]2(CC[C@@H]3CN(C(=O)c4cccc5ncccc45)C[C@@H]32)Nc2ccccc21] |
| 58 | 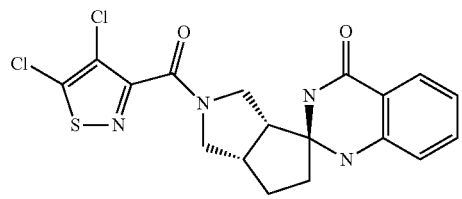 [SMILES: O=C1N[C@]2(CC[C@@H]3CN(C(=O)c4nsc(Cl)c4Cl)C[C@@H]32)Nc2ccccc21] |
| 59 | 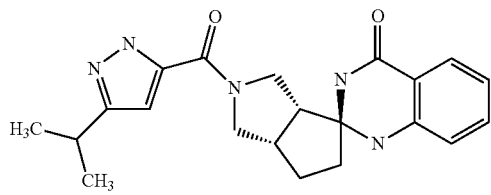 [SMILES: CC(C)c1cc(C(=O)N2C[C@H]3CC[C@]4(NC(=O)c5ccccc5N4)[C@H]3C2)[nH]n1] |
| Example No. | COMPOUND |
|---|---|
| 60 | 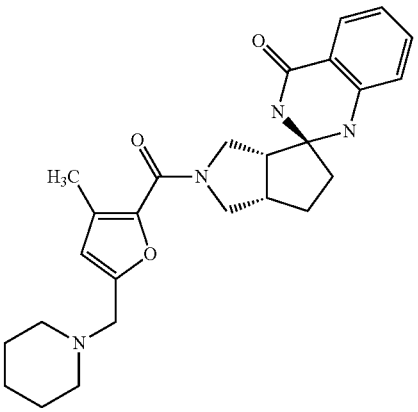 [SMILES: Cc1cc(CN2CCCCC2)oc1C(=O)N1C[C@H]2CC[C@]3(NC(=O)c4ccccc4N3)[C@H]2C1] |
| 61 | 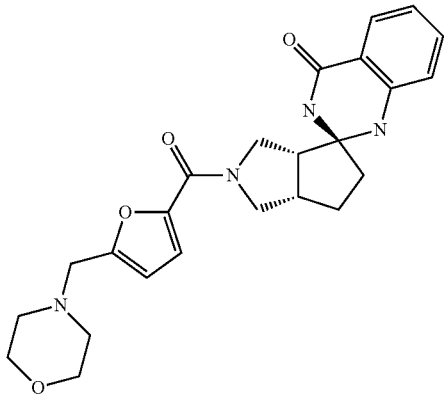 [SMILES: O=C1N[C@]2(CC[C@@H]3CN(C(=O)c4ccc(CN5CCOCC5)o4)C[C@@H]32)Nc2ccccc21] |
| 62 | 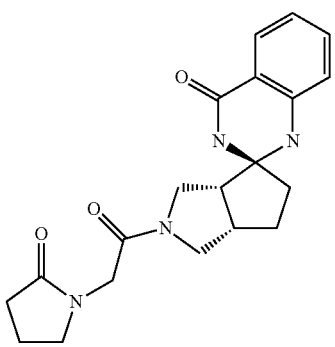 [SMILES: O=C1N[C@]2(CC[C@@H]3CN(C(=O)CN4CCCC4=O)C[C@@H]32)Nc2ccccc21] |
| 63 | 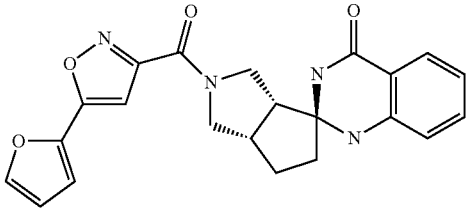 [SMILES: O=C1N[C@]2(CC[C@@H]3CN(C(=O)c4cc(-c5ccco5)on4)C[C@@H]32)Nc2ccccc21] |

-continued
| Example No. | COMPOUND |
|---|---|
| 64 | 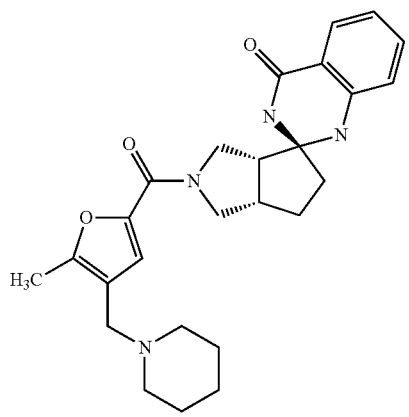 [SMILES: Cc1oc(C(=O)N2C[C@H]3CC[C@]4(NC(=O)c5ccccc5N4)[C@H]3C2)cc1CN1CCCCC1] |
| 65 | 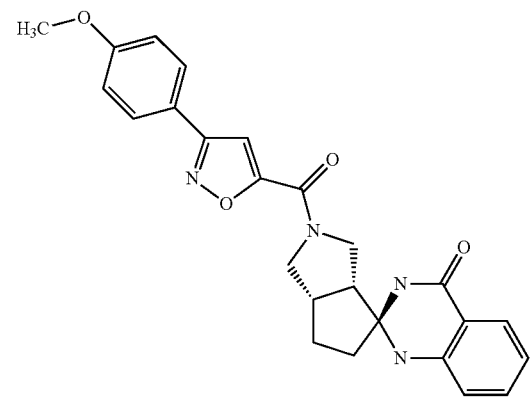 [SMILES: COc1ccc(-c2cc(C(=O)N3C[C@H]4CC[C@]5(NC(=O)c6ccccc6N5)[C@H]4C3)on2)cc1] |
| 66 | 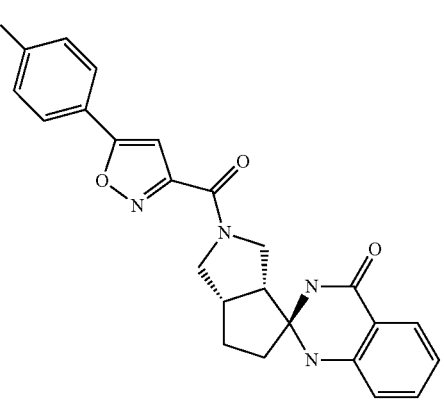 |
-continued
| Example No. | COMPOUND |
|---|---|
| 67 | 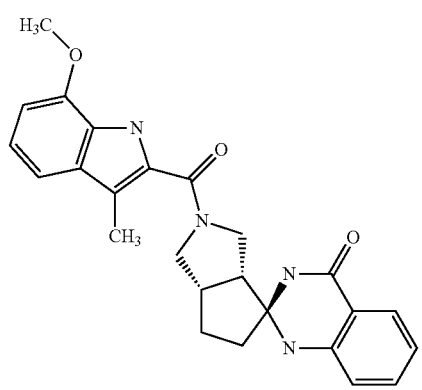 [SMILES: COc1cccc2c(C)c(C(=O)N3C[C@H]4CC[C@]5(NC(=O)c6ccccc6N5)[C@H]4C3)[nH]c12] |
| 68 | 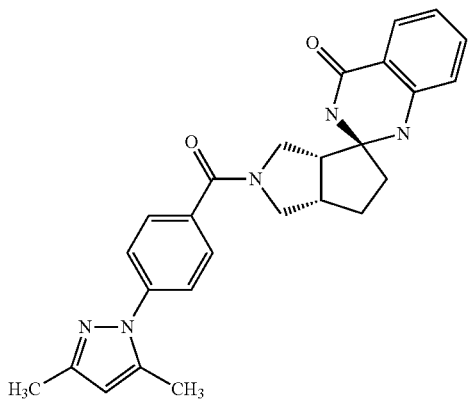 [SMILES: Cc1cc(C)n(-c2ccc(C(=O)N3C[C@H]4CC[C@]5(NC(=O)c6ccccc6N5)[C@H]4C3)cc2)n1] |
| 69 | 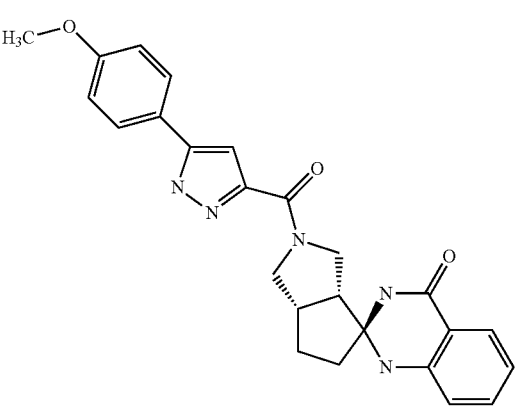 [SMILES: COc1ccc(-c2cc(C(=O)N3C[C@H]4CC[C@]5(NC(=O)c6ccccc6N5)[C@H]4C3)n[nH]2)cc1] |
| 70 | 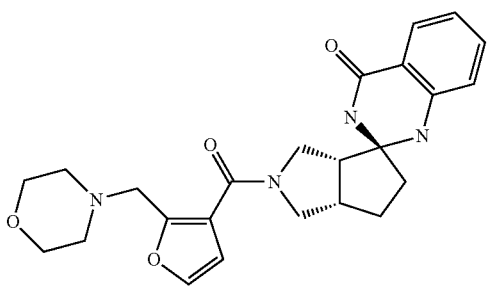 [SMILES: O=C1N[C@]2(CC[C@@H]3CN(C(=O)c4ccoc4CN4CCOCC4)C[C@@H]32)Nc2ccccc21] |

| Example No. | COMPOUND |
|---|---|
| 71 | 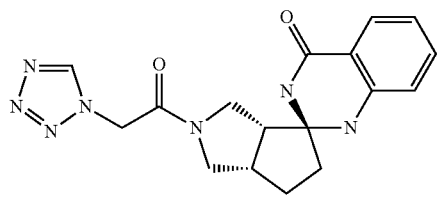 [SMILES: O=C1N[C@]2(CC[C@@H]3CN(C(=O)Cn4cnnn4)C[C@@H]32)Nc2ccccc21] |
| 72 | 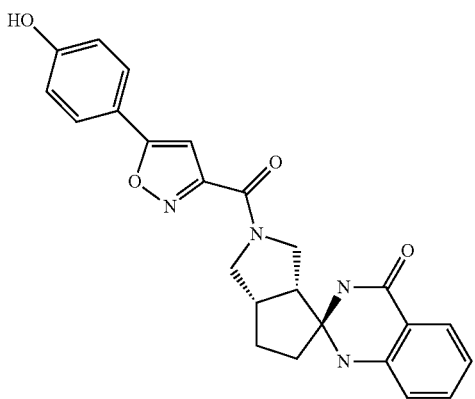 [SMILES: O=C1N[C@]2(CC[C@@H]3CN(C(=O)c4cc(-c5ccc(O)cc5)on4)C[C@@H]32)Nc2ccccc21] |
| 73 | 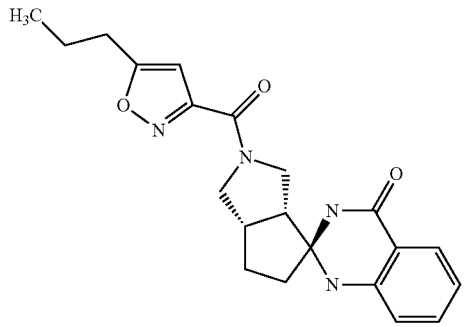 [SMILES: CCCc1cc(C(=O)N2C[C@H]3CC[C@]4(NC(=O)c5ccccc5N4)[C@H]3C2)no1] |
| 74 | 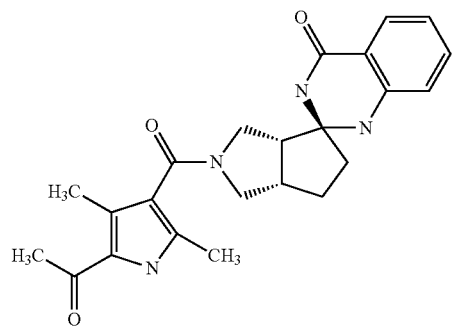 [SMILES: CC(=O)c1[nH]c(C)c(C(=O)N2C[C@H]3CC[C@]4(NC(=O)c5ccccc5N4)[C@H]3C2)c1C] |
| Example No. | COMPOUND |
|---|---|
| 75 | 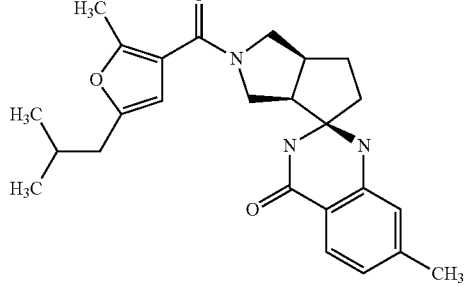 |
| 76 | 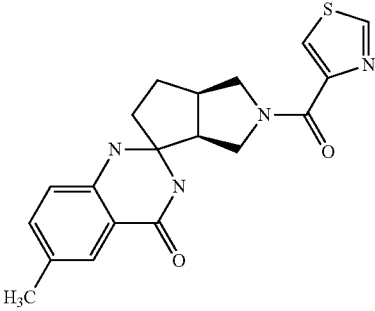 [SMILES: Cc1ccc2c(c1)C(=O)NC1(CC[C@H]3CN(C(=O)c4cscn4)C[C@H]31)N2] |
| 77 | 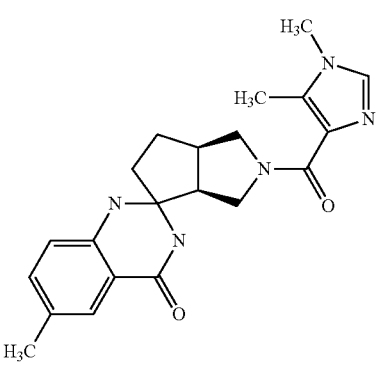 [SMILES: Cc1ccc2c(c1)C(=O)NC1(CC[C@H]3CN(C(=O)c4ncn(C)c4C)C[C@H]31)N2] |
| 78 | 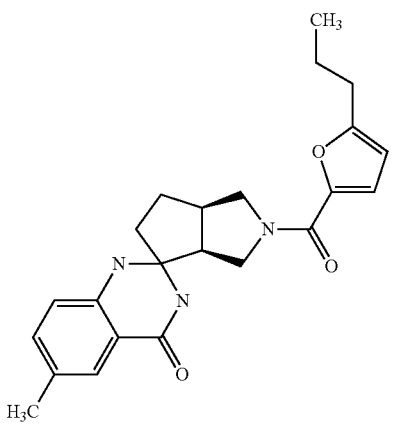 [SMILES: CCCc1ccc(C(=O)N2C[C@@H]3CCC4(NC(=O)c5cc(C)ccc5N4)[C@@H]3C2)o1] |

| Example No. | COMPOUND |
|---|---|
| 79 | 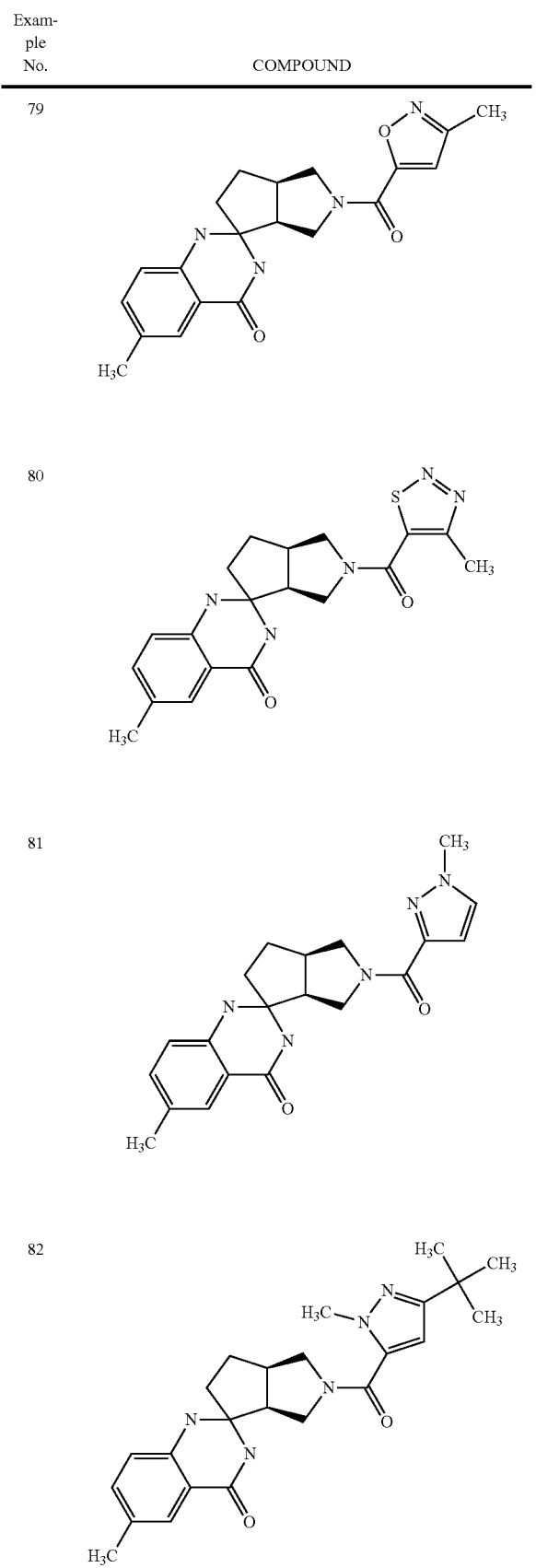 |
| 80 | |
| 81 | |
| 82 | |
| Example No. | COMPOUND |
|---|---|
| 83 | 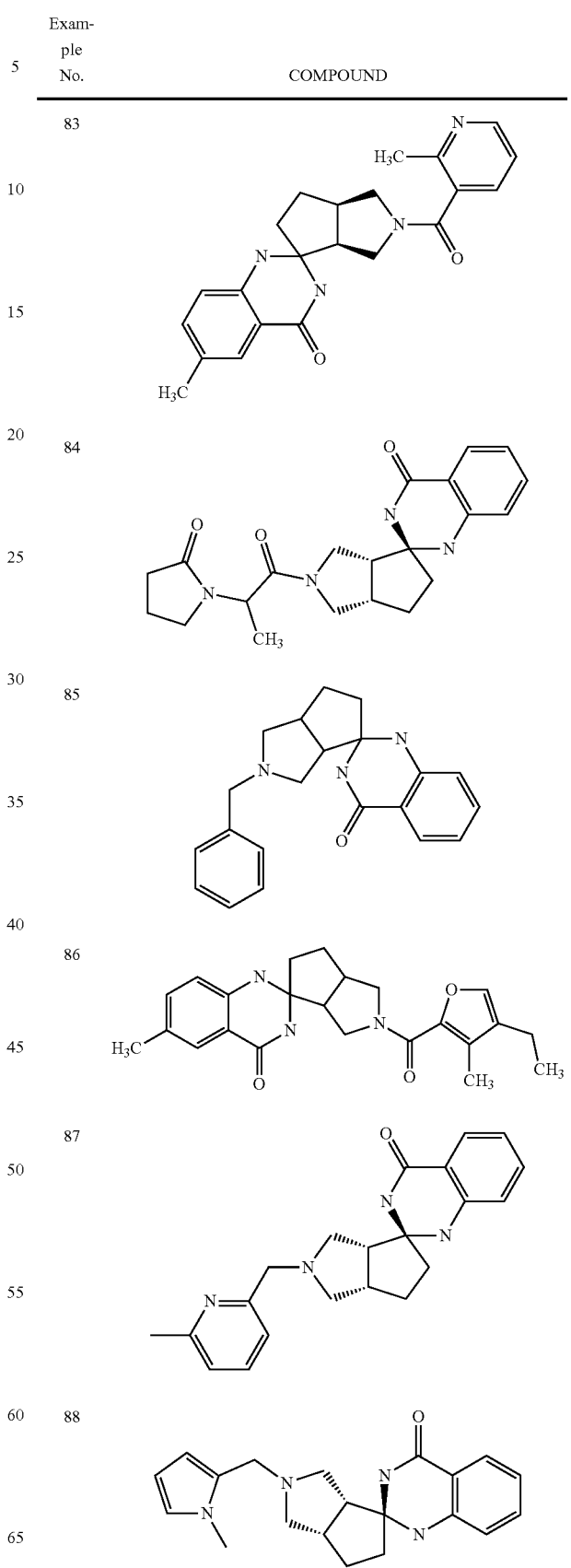 |
| 84 | |
| 85 | |
| 86 | |
| 87 | |
| 88 | |

| Example No. | COMPOUND |
|---|---|
| 89 | 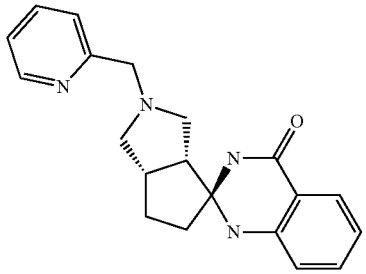 [SMILES: O=C1N[C@]2(CC[C@@H]3CN(Cc4ccccn4)C[C@@H]32)Nc2ccccc21] |

| Example No. | COMPOUND |
|---|---|
| 90 | 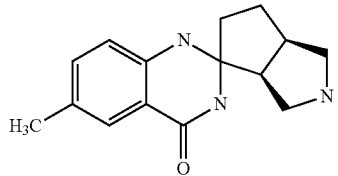 [SMILES: Cc1ccc2c(c1)C(=O)NC1(CC[C@H]3CNC[C@H]31)N2] |

In each of the compounds in the preceding Table, it is to be understood that each atom includes a full valence, where the remaining atoms are hydrogens.

What is claimed is:

1. A unit dose or unit dosage form for treating a viral infection, the unit dose or unit dosage form comprising
   (a) a therapeutically effective amount of one or more compounds of the formula

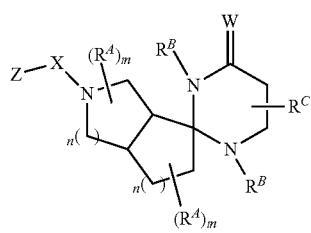

or a pharmaceutically acceptable salt thereof, wherein
   X is carbonyl, alkylene, or alkylenecarbonyl;
   Z is aryl, or heteroaryl, each of which is optionally substituted;
   W is O or S;
   Each $R^A$ is H, where m is independently selected in each instance from the group consisting of 1, 2, and 3;
   Each $R^B$ is H;
   $R^C$ represents a fused aryl, or heteroaryl, each of which is optionally substituted; and
   n is independently selected in each instance from the group consisting of 1, 2, and 3; and
   (b) one or more pharmaceutically acceptable carriers, diluents, or excipients, or a combination thereof.

2. The composition of claim 1 wherein X is carbonyl.

3. The composition of claim 1 wherein X is (1-3C)alkylenecarbonyl in which Z is attached to the alkylene portion.

4. The composition of claim 1 wherein X is alkylene.

5. The composition of claim 1 wherein X is methylene.

6. The composition of claim 1 wherein Z is monocyclic aryl or heteroaryl, each of which is optionally substituted.

7. The composition of claim 1 wherein Z is bicyclic aryl or heteroaryl, each of which is optionally substituted.

8. The composition of claim 1 wherein W is O.

9. The composition of claim 1 wherein $R^C$ represents a fused optionally substituted aryl.

10. The composition of claim 1 wherein n is 1 in each instance.

11. The composition of claim 1 wherein the compound has the following relative stereochemistry

12. The composition of claim 1 wherein the compound has the following absolute stereochemistry

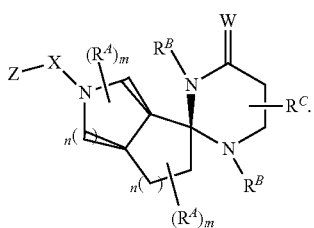

13. The composition of claim 10 which is a compound of the following formula and which has the following relative stereochemistry

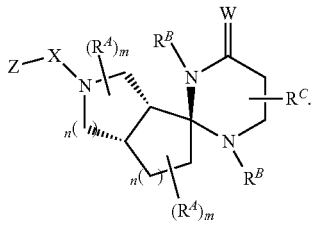

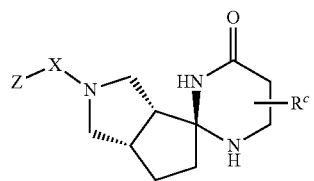

wherein X is methylene or carbonyl; and $R^c$ is a fused benzene ring which may bear a methyl substituent.

14. The composition of claim 13 wherein the compound has the following relative stereochemistry

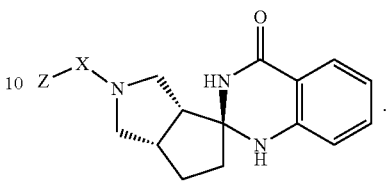

15. The composition of claim 13 wherein X is methylene.

16. The composition of claim 13 wherein X is carbonyl.

17. The composition of claim 15 wherein Z is monocyclic aryl or heteroaryl, each of which is optionally substituted.

18. The composition of claim 15 wherein Z is bicyclic aryl or heteroaryl, each of which is optionally substituted.

19. A method for treating a viral infection in a patient, the method comprising the step of administering to the patient a therapeutically effective amount of one or more compounds of claim 1, or a therapeutically effective amount of one or more composition of claim 1, wherein the viral infection is a hepatitis C infection.

\* \* \* \* \*